(12) United States Patent
Ice et al.

(10) Patent No.: US 11,237,410 B2
(45) Date of Patent: Feb. 1, 2022

(54) ELECTRONICS ASSEMBLY FOR USE IN ELECTRONIC CONTACT LENS

(71) Applicant: Tectus Corporation, Saratoga, CA (US)

(72) Inventors: Donald Arthur Ice, Milpitas, CA (US); Benjamin Lyle Hackett, Saratoga, CA (US)

(73) Assignee: Tectus Corporation, Saratoga, CA (US)

( * ) Notice: Subject to any disclaimer, the term of this patent is extended or adjusted under 35 U.S.C. 154(b) by 190 days.

(21) Appl. No.: 16/554,399

(22) Filed: Aug. 28, 2019

(65) Prior Publication Data

US 2021/0063773 A1 Mar. 4, 2021

(51) Int. Cl.
  *G02C 7/04*   (2006.01)
  *G02C 11/00*  (2006.01)
  *H05K 1/18*   (2006.01)
  *H05K 1/02*   (2006.01)
  *A61F 2/16*   (2006.01)

(52) U.S. Cl.
  CPC .......... *G02C 11/10* (2013.01); *A61F 2/1627* (2013.01); *G02C 7/049* (2013.01); *H05K 1/0281* (2013.01); *H05K 1/181* (2013.01); *H05K 1/189* (2013.01); *H05K 1/186* (2013.01); *H05K 2201/1003* (2013.01); *H05K 2201/10151* (2013.01)

(58) Field of Classification Search
  CPC ....... G02C 11/10; G02C 7/049; A61F 2/1627; H05K 1/0281; H05K 1/181; H05K 1/189; H05K 1/186; H05K 2201/1003; H05K 2201/10151
  See application file for complete search history.

(56) References Cited

U.S. PATENT DOCUMENTS

| | | | |
|---|---|---|---|
| 5,682,210 A | 10/1997 | Weirich | |
| 6,544,193 B2 * | 4/2003 | Abreu | A61B 3/10 600/558 |
| 8,721,074 B2 | 5/2014 | Pugh | |
| 8,786,675 B2 | 7/2014 | Deering | |
| 9,009,958 B2 | 4/2015 | Etzkorn | |
| 9,977,256 B2 * | 5/2018 | Pugh | G02C 7/083 |
| 2009/0204207 A1 | 8/2009 | Blum | |
| 2009/0279050 A1 | 11/2009 | McGinn | |
| 2010/0076553 A1 | 3/2010 | Pugh | |
| 2010/0103368 A1 | 4/2010 | Amirparviz | |
| 2013/0135578 A1 | 5/2013 | Pugh | |
| 2013/0194540 A1 * | 8/2013 | Pugh | G02C 7/04 351/159.03 |
| 2013/0258275 A1 | 10/2013 | Toner | |
| 2014/0273316 A1 | 9/2014 | Pugh | |

(Continued)

OTHER PUBLICATIONS

International Search Report and Written Opinion for App. No. PCT/US2020/048286, dated Oct. 6, 2020, 16 pages.

*Primary Examiner* — Binh B Tran

(74) *Attorney, Agent, or Firm* — Fenwick & West LLP

(57) ABSTRACT

A substrate carries electrical components. It is bent into a non-planar shape to fit into a contact lens. For example, the substrate may be constructed from a flexible circuit board. The circuit board has certain regions for mounting electrical components. The flexible circuit board is bent into a three-dimensional shape that fits into the contact lens. The regions used to mount electrical components remain flat.

23 Claims, 13 Drawing Sheets

(56) References Cited

U.S. PATENT DOCUMENTS

| | | |
|---|---|---|
| 2016/0274377 A1* | 9/2016 | Toner .................... G02C 7/083 |
| 2017/0176774 A1 | 6/2017 | Linhardt |
| 2018/0045980 A1 | 2/2018 | Linhardt |
| 2018/0104921 A1 | 4/2018 | Beyad |
| 2019/0011809 A1 | 1/2019 | Wippermann |
| 2019/0094981 A1 | 3/2019 | Bradski |
| 2019/0109536 A1 | 4/2019 | Lee |
| 2019/0243130 A1 | 8/2019 | Lamkin |

* cited by examiner

ELECTRONICS ASSEMBLY FOR USE IN ELECTRONIC CONTACT LENS

BACKGROUND

1. Technical Field

This disclosure relates generally to contact lenses that contain electrical components and more particularly to assemblies that carry the electrical components within the contact lens.

2. Description of Related Art

Contact lenses that provide refractive vision correction are commonplace. Recently, there has been increased interest in contact lenses that perform functions other than just vision correction. In many of these applications, a contact lens may carry a payload for performing various functions. For example, a contact lens may contain a payload of one or more electrical components, such as projectors, imaging devices (imagers), sensors, coils, batteries, MEMS (micro-electro-mechanical systems), accelerometers and magnetometers, etc. These contact lenses may be referred to as electronic contact lenses.

An electronic contact lens has some structure to support the different electrical components and to provide electrical connections between the different components. However, the form factor of such a structure is significantly limited because it must fit in the contact lens. The contact lens has a limited thickness and volume and it is inherently curved rather than planar. Furthermore, light enters the eye through the center of the contact lens. In order to avoid blocking this incoming light, the structure would have to be located outside the center region of the contact lens. This further limits the possible designs of the supporting structure.

As a result, it can be challenging to provide a support and interconnect structure for electrical components, while still meeting the other requirements of the contact lens.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

A contact lens may contain payloads for performing various functions. For example, a contact lens may contain electrical components such as projectors, imaging devices, sensors, coils, batteries, MEMS (micro-electro-mechanical systems), accelerometers and magnetometers, gyroscopes, etc. The electrical components are contained within the limited space of the contact lens and typically must also have electrical connections such as for power, control and data. Furthermore, many electrical components, such as semiconductor devices, are designed to be mounted to a flat surface, while contact lenses are inherently curved.

In one approach, a substrate bent into a non-planar shape is used to carry the electrical components. For example, the substrate may be constructed from a flexible circuit board that is bent into a three-dimensional shape that fits inside an electronic contact lens. The bent circuit board has certain regions which are flat for mounting the electrical components. The bending to create the three-dimensional shape occurs between the flat regions. The components may be mounted to the circuit board, such as by surface mounting or flip-chip mounting of semiconductor devices, before the circuit board is bent into shape.

In one design, the circuit board is bent into the shape of a band with flat facets. Bending between the facets creates a non-planar annular shape (for example, a many-sided frustum) that fits inside the electronic contact lens. The facets themselves remain flat to provide flat surfaces for mounting electrical components.

In another design, the circuit board has a flat annular core portion, with flat tabs that extend radially from the flat annular core. The annular core portion fits inside the contact lens without bending. Bending between the flat tabs and the core portion create a non-planar shape that fits inside the contact lens, while leaving the tabs flat in order to provide flat surfaces for mounting electrical components.

Figure 1A:
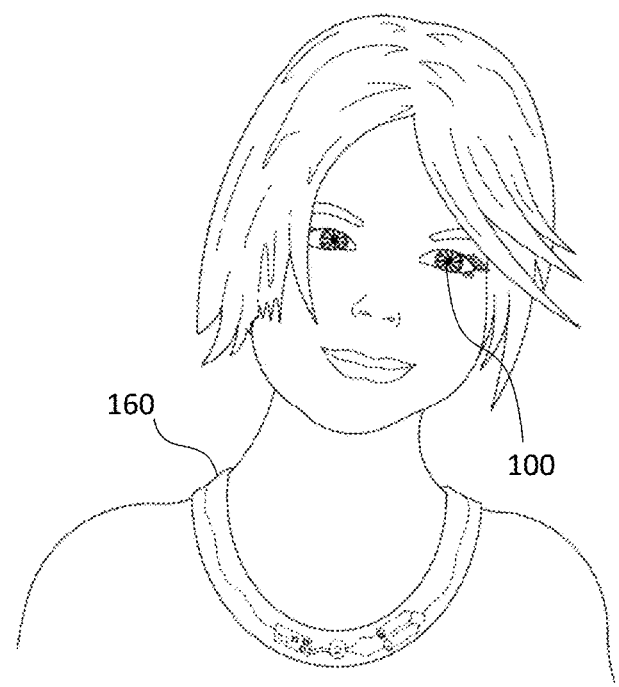
FIG. 1A shows a user wearing a display mounted in a contact lens.
Figure 1B:
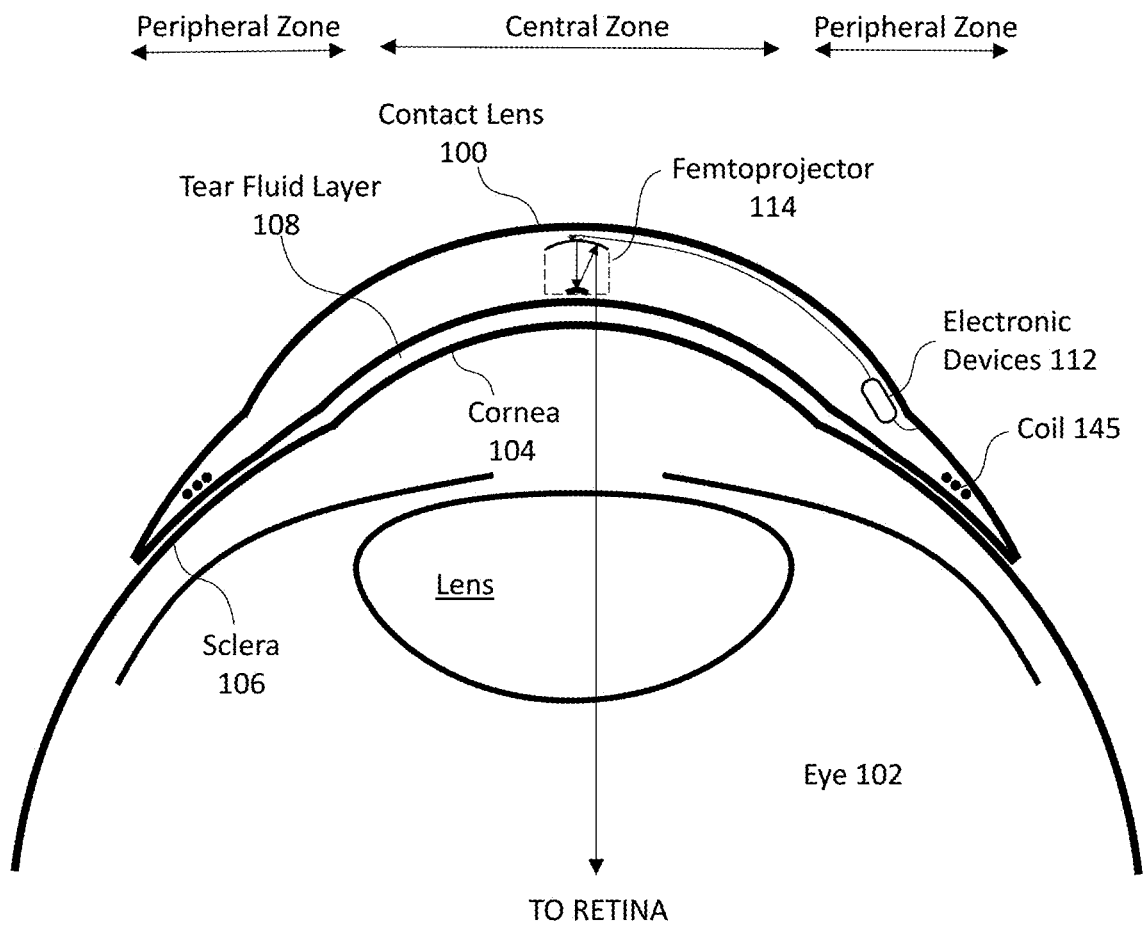
FIG. 1B shows a cross sectional view of the contact lens display mounted on the user's eye.

Further details are provided using an eye-mounted display as an example of an electronic contact lens, although it should be understood that other types of electronic contact lenses may also be produced. FIG. 1A shows a user wearing a display mounted in a scleral contact lens 100. FIG. 1A also shows an accessory necklace 160, which is discussed with FIG. 2. FIG. 1B shows a cross sectional view of the scleral contact lens 100 mounted on the user's eye. Scleral contact lenses are designed to not move around on the wearer's eye. The eye 102 includes a cornea 104 and a sclera 106. The scleral contact lens 100 is supported by the sclera 106 and vaults over the cornea 104. A tear fluid layer 108 may be formed between the contact lens 100 and the cornea 104. Oxygen permeates through the contact lens 100 to the cornea 104.

The contact lens 100 contains payload(s). For example, the payload(s) may include electronics, including electronics that require a power source such as a battery or a coil that is inductively powered. In the example of FIG. 1, the payloads include a small projector that projects images onto the wearer's retina (referred to as a femtoprojector 114), and the corresponding electronics 112 to operate the femtoprojector. These are powered by the receiver coil 145, which is positioned around the periphery of the contact lens. The femtoprojector 114 may include an LED frontplane with an LED array, an ASIC backplane with electronics that receives the data to drive the LED frontplane, and optics to project light from the LED array onto the retina. The femtoprojector 114 preferably fits into a 2 mm by 2 mm by 2 mm volume or even into a 1 mm by 1 mm by 1 mm volume.

The femtoprojector 114 is positioned over the cornea since it projects images onto the retina. The electronics 112 may be positioned away from the cornea, as shown in FIG. 1B. For convenience, the contact lens 100 is divided into a central zone and a peripheral zone. The central zone overlaps the cornea 104. The area outside the cornea is part of the peripheral zone. In FIG. 1, the femtoprojector 114 is located within the central zone of the contact lens because it projects images into the user's eye, while the electronics 112 and coil 145 are located in the peripheral zone. Because people have eyes of different sizes and shapes, for convenience, the central zone may be defined as the 10 mm diameter center area of the contact lens (i.e., within 5 mm radius of the central axis of the contact lens). The diameter of the boundary between the cornea and the sclera is typically 10-12.5 mm. Payload components that project light onto the retina typically will be located within the central zone due to the required optical path. Conversely, payload components that do not project light onto the retina or otherwise interact with the retina may be located on the edge of the central zone or outside the central zone so that they do not block light from reaching the retina.

Other examples of powered payloads include sensors, imagers, and eye tracking components such as accelerometers, gyroscopes and magnetometers. Payloads may also include passive devices, such as a coil or antenna for wireless power or data transmission, capacitors for energy storage, and passive optical structures (e.g., absorbing light baffles, beam-splitters, imaging optics). The contact lens 100 may also contains multiple femtoprojectors, each of which projects images onto the user's retina. The contact lens 100 moves with the user's eye 102 as the user's eye rotates in its socket. Because the femtoprojectors are mounted in the contact lens 100, they also move with the user's eye and project to the same region of the retina. Some femtoprojector(s) may always project images to the fovea, and other femtoprojector(s) may always project images to more peripheral regions which have lower resolutions. As a result, different femtoprojectors may have different resolutions. The images from different femtoprojectors may be overlapping, to form a composite image on the wearer's retina.

With respect to the contact lens, terms such as "top", "front", "outer" and "anterior" refer to the direction away from the wearer's eye, while "bottom", "rear" "inner" and "posterior" refer to the direction towards the wearer's eye.

Figure 2:
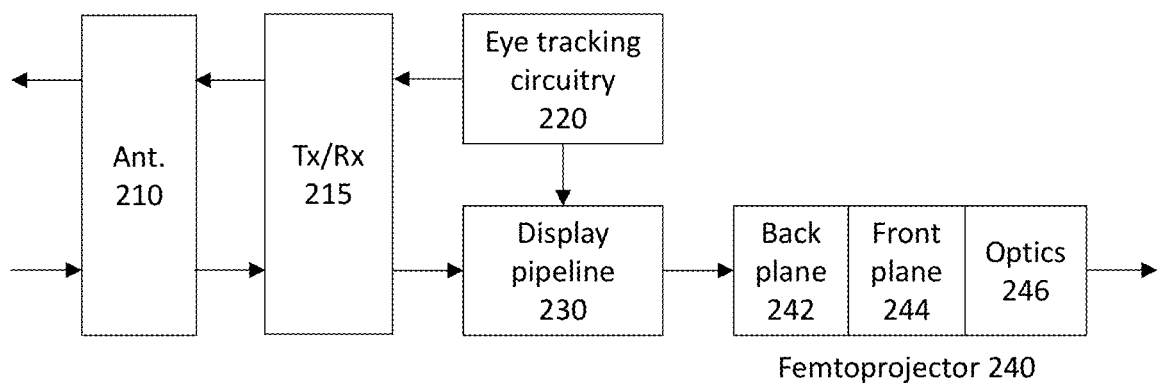
FIG. 2 is a functional block diagram of an eye-mounted display using a contact lens.
Figure 2:
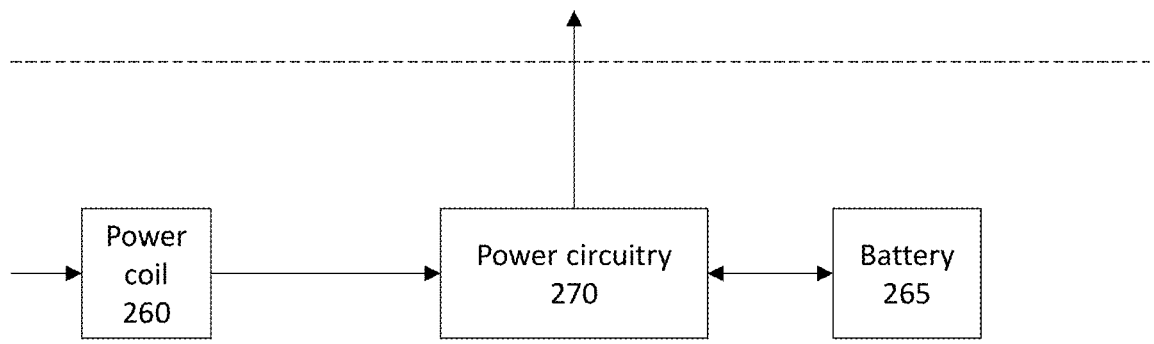

FIG. 2 is a functional block diagram of an eye-mounted display using the scleral contact lens described above. The display can be divided into a data/control subsystem 200 and a power subsystem 250.

In this example, the receive path of the data/control subsystem 200 includes an antenna 210, receiver circuitry 215, a data pipeline 230, and a femtoprojector 240. Data from an external source is wirelessly transmitted to the display and received via the antenna 210. The receiver circuitry 215 performs the functions for receiving the data, for example demodulation, noise filtering, and amplification. It also converts the received signals to digital form. The pipeline 230 processes the digital signals for the femtoprojector 240. These functions may include decoding, and timing. The processing may also depend on other signals generated internally within the contact lens, for example eye tracking sensors 220 or ambient light sensing. The femtoprojector 240 then projects the corresponding images onto the wearer's retina. In this example, the femtoprojector 240 includes a CMOS ASIC backplane 242, LED frontplane 244 and optics 246.

The data/control subsystem 200 may also include a back channel through transmitter circuitry 215 and antenna 210. For example, the contact lens may transmit eye tracking data, control data and/or data about the status of the contact lens.

Power is received wirelessly via a power coil 260. This is coupled to circuitry 270 that conditions and distributes the incoming power (e.g., converting from AC to DC if needed). The power subsystem 250 may also include energy storage devices, such as batteries 265 or capacitors.

In addition to the components shown in FIG. 2, the overall system may also include components that are outside the contact lens (i.e., off-lens). For example, head tracking and eye tracking functions may be performed partly or entirely off-lens. The data pipeline may also be performed partially or entirely off-lens. Each of the arrows on the lefthand side of FIG. 2 also connects to an off-lens component. The power transmitter coil is off-lens, the source of image data and control data for the contact lens display is off-lens, and the receive side of the back channel is off-lens.

There are many ways to implement the different system functions. Some portions of the system may be entirely external to the user, while other portions may be worn by the user in the form of a headpiece or glasses. For example, see U.S. patent application Ser. No. 16/530,949, "Headgear Providing Inductive Coupling To A Contact Lens," (41898), which is incorporated by reference in its entirety. Components may also be worn on a belt, armband, wrist piece, necklace, or other types of packs. FIG. 1A shows an example where some functionality is implemented in a necklace 160 worn by the user. In this example, the necklace 160 includes a wireless transmitter that communicates with the eye-mounted display 100.

Figure 3A:
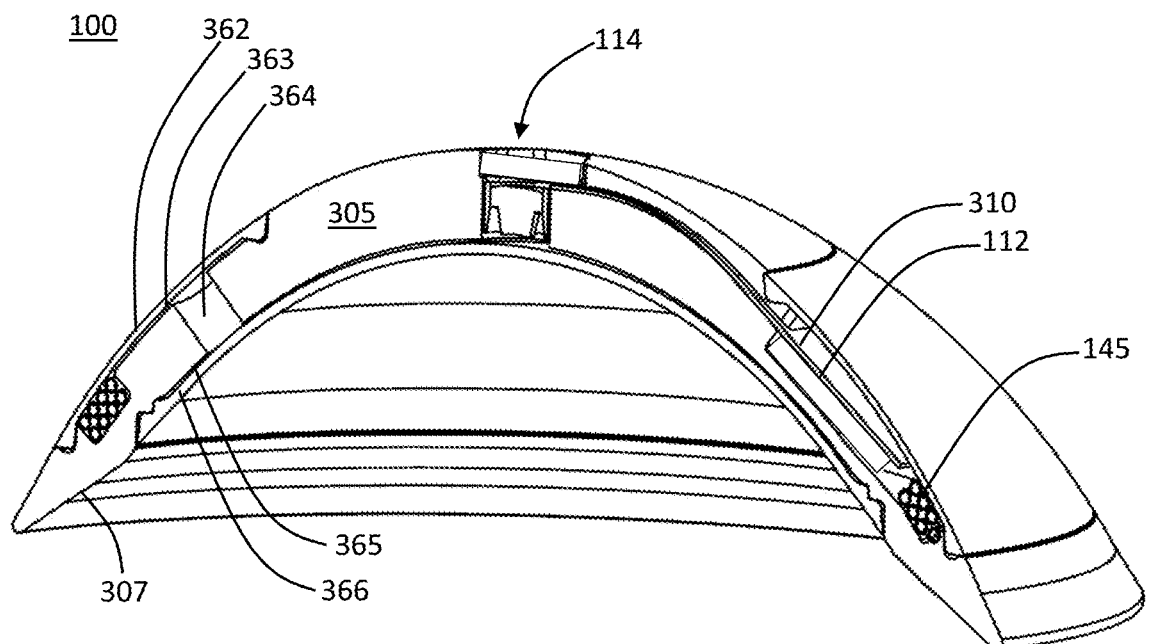
FIGS. 3A and 3B are cross-sectional views of an electronic contact lens containing an electronics assembly with a non-planar substrate.
Figure 3B:
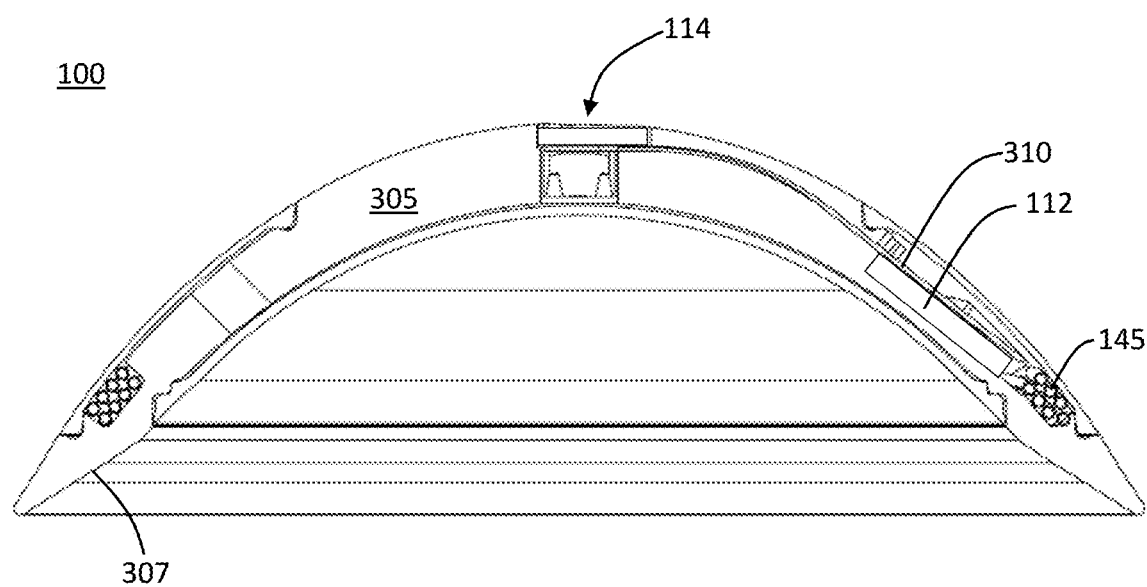

FIGS. 3A and 3B are cross-sectional views of an electronic contact lens 100 containing an electronics assembly with a non-planar substrate. The scleral contact lens 100 includes a core 305. The core 305 has a base surface 307 that mounts to the sclera of the eye. The core 305 also contains the payload(s). In this example, the payloads include the femtoprojector 114 and electronics 112 (and interconnects between them) and coil 145 from FIG. 1, as well as other components. The femtoprojector 114 is positioned in a central zone of the contact lens because it projects images onto the user's retina. The electronics 112 and coil 145 are positioned in the periphery of the contact lens, so that they do not block light entering the user's eye.

Electrical components are mounted on a non-planar substrate 310, which positions the components and provides electrical connections between the components. The non-planar substrate 310 is initially fabricated as a planar substrate and then bent into a three-dimensional shape that fits inside the contact lens. The three-dimensional shape includes flat facets that carry the electrical components. The electrical components may be mounted onto the substrate and tested while the substrate is still flat. For example, the non-planar substrate may be a flexible circuit board, which also contains conductive traces that provide electrical connections between the components. In some designs, the flat facets are arranged in a band. Bending between adjacent facets in the band forms the three-dimensional shape. After bending, the band of facets may have a three-dimensional annular shape. The entire electronics assembly, including substrate and components, may be encapsulated within the core 305. Further description is provided in FIGS. 4-6.

FIGS. 3A-3B also show structures that allow oxygenation of the user's cornea. The contact lens 100 also includes a gas-permeable outer covering 362 and a gas-permeable inner covering 366. Each covering 362, 366 forms a corresponding air gap 363, 365 between the covering and the core 305. One or more air shaft(s) 364 through the core 305 connects the two air gaps 363, 365. This provides a path for oxygen to reach the user's cornea. For example, see U.S. patent application Ser. No. 16/360,872, "Oxygen Permeable Scleral Contact Lenses With Thick Payloads," (41902), which is incorporated by reference in its entirety.

Figure 4A:
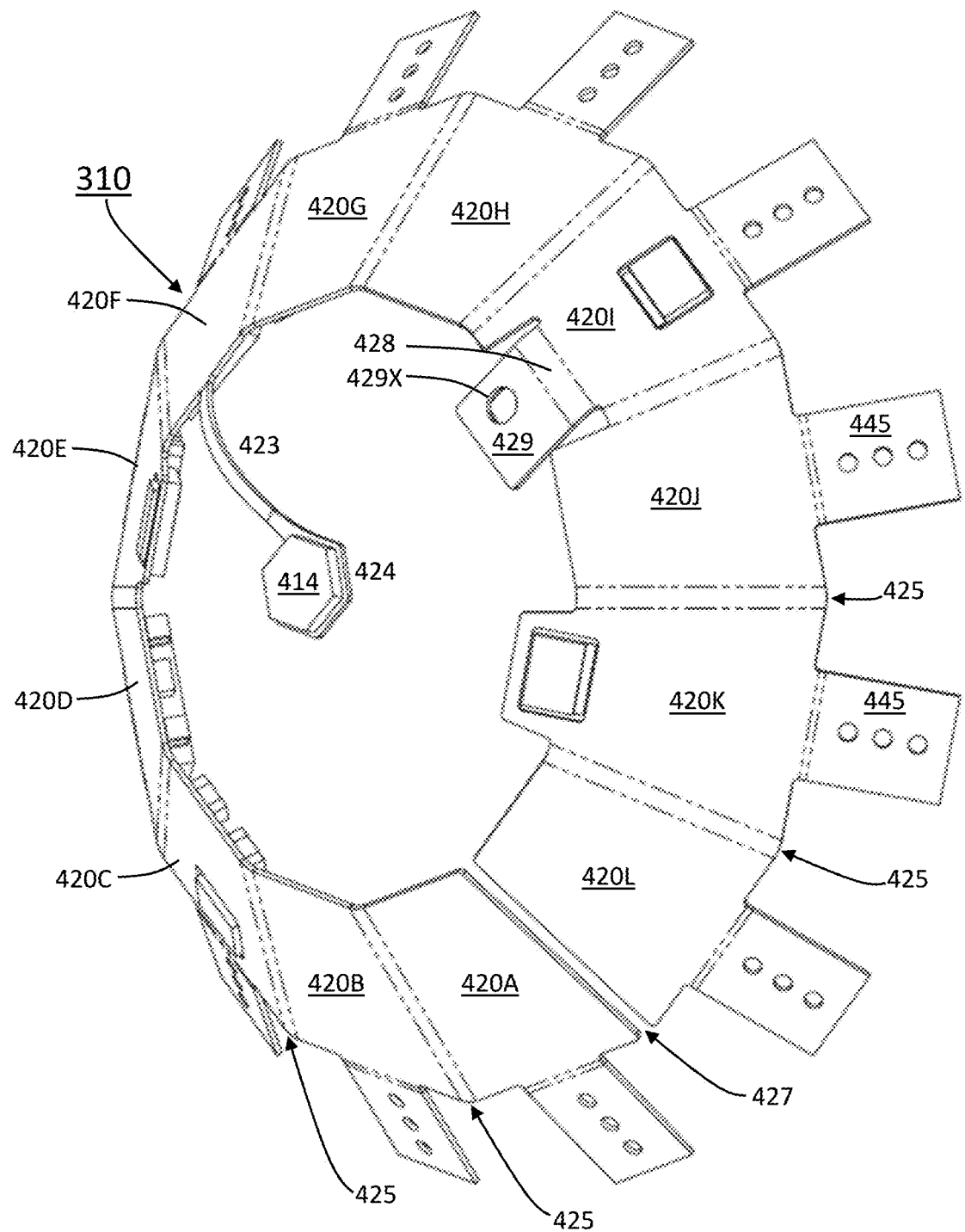
FIGS. 4A and 4B are anterior and posterior perspective views showing the electronics assembly of FIG. 3.
Figure 4B:
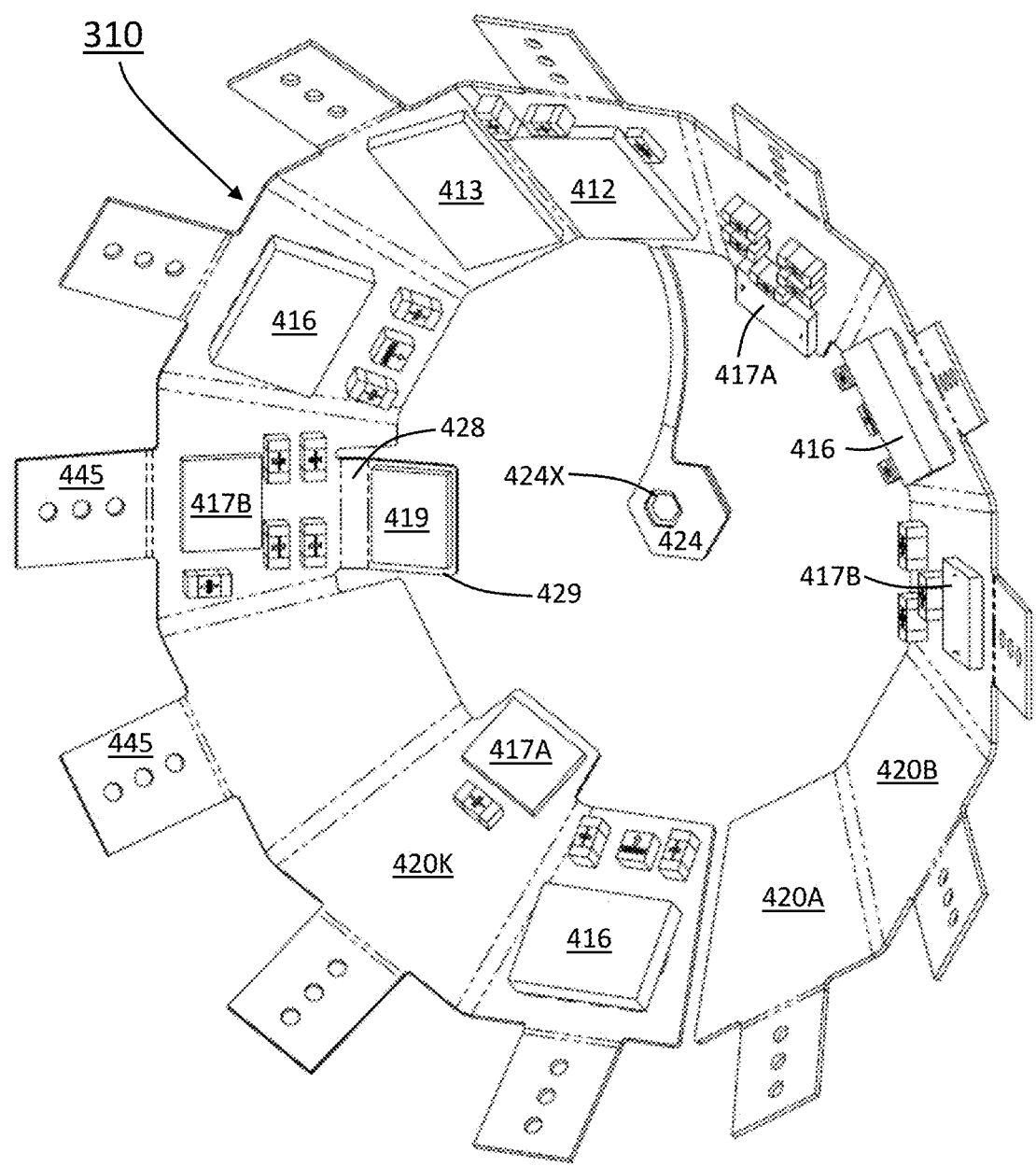

FIGS. 4A and 4B are anterior and posterior perspective views showing the non-planar substrate 310 and electrical components of the electronics assembly of FIG. 3. The electronics assembly is approximately dome-shaped in order to fit into the contact lens. In the anterior view of FIG. 4A, the center of the dome-shaped assembly is close to the viewer and the perimeter of the dome is away from the viewer. The surfaces shown in FIG. 4A face away from the wearer's eye when the contact lens is worn. The posterior view of FIG. 4B shows a view from inside the dome. The perimeter of the dome is close to the viewer and the center of the dome is away from the viewer. The surfaces shown in FIG. 4B face towards the wearer's eye.

Figure 5:
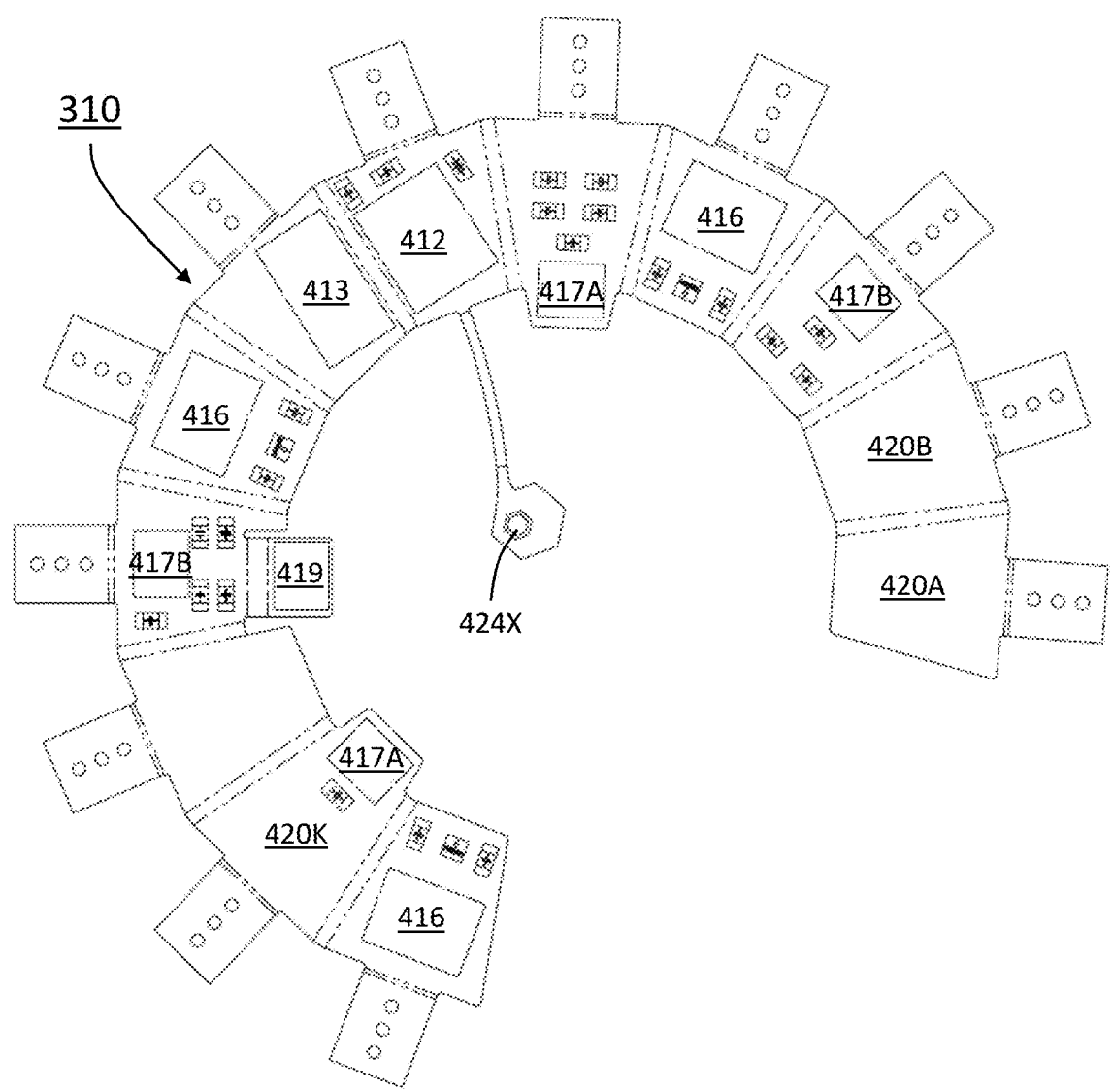
FIG. 5 is a posterior view of the electronics assembly of FIG. 3 before folding.

This particular substrate 310 design has a band of twelve flat facets 420A-L. The facets are labelled A-L, where facet 420A is on one end of the band and facet 420L is at the opposite end of the band. For clarity, not every facet is labeled in every figure. Two planes intersect in a line, so adjacent facets 420A and 420B meet at an edge region 425, which is bendable. Facets 420B and 420C also meet at a bendable edge region 425, and so on. Facets 420L and 420A do not meet. There is a gap 427 between facets 420L and 420A, as shown in FIG. 5.

In this example, the band formed by the twelve facets 420 is part of a regular 12-sided frustum. The band of facets is opaque but is positioned such that the band does not substantially block light from entering the eye through the contact lens. In this example, most of the semiconductor devices are mounted on the bottom (posterior surface) of each facet, as shown in FIG. 4B. The facets 420 may be different sizes and/or shapes to accommodate different components. In these figures, positions may be described using a cylindrical coordinate system. "Height" or "z" refers to the direction along the central axis of the contact lens. "Radius" or "r" refers to the radial direction outward from the central axis. Because of the shape of the contact lens, radius and height are not independent. "Azimuth" or "arc" or "θ" is the angular direction in the plane perpendicular to the z-direction.

In the example of FIG. 4B, the components include three magnetometers 416 and four accelerometers 417A-B, which are used for eye tracking. These sensor chips are mounted at specific angles to each other to allow sensing along linearly independent spatial axes. For example, see U.S. patent application Ser. No. 16/005,379, "Contact Lens-Based Eye Tracking," (38838), which is incorporated by reference in its entirety. The twelve facets form substantially a full annulus so each facet subtends 360/12=30 degrees of arc. With this layout, four components placed on every third facet are spaced 90 degrees apart, and three components placed on every fourth facet are spaced 120 degrees apart. The magnetometers 416 are mounted on every fourth facet 420D, H and L, so that they are spaced 120 degrees apart and they are all approximately the same radial distance from the center of the contact lens.

There are two pairs of accelerometers 417A and 417B. One pair of accelerometers 417A is mounted on diametrically opposing facets 420E and K, in order to increase the distance between them. Similarly, the other pair 417B is mounted on diametrically opposing facets 420C and I. In this configuration, the two pairs of accelerometers are not spaced 90 degrees apart, but no two of the accelerometers are mounted on adjacent facets. In an alternative design, the accelerometers may be mounted on every third facet instead of the configuration shown. Radially, the pair 417B is mounted at a larger radius towards the perimeter of the band of facets while the pair 417A is mounted more towards the center of the band, in order to increase the vertical separation between the two pairs. In fact, facets 420E and K are extended towards the center to increase this separation. If additional extension is desired, additional bending may be introduced to conform to the contact lens shape. See the discussion of facet 4201 below.

The electronics assembly of FIG. 4B also includes semiconductor devices 414 for the femtoprojector. The optics of the femtoprojector are not shown in FIG. 4B, but devices 414 include the ASIC backplane and LED frontplane for the femtoprojector. For example, see U.S. patent application Ser. No. 16/034,761, "Advanced Optical Designs for Eye-Mounted Imaging Systems," (40785); Ser. No. 15/892,891, "Backplane for Eye-Mounted Display," (37916); and Ser. No. 16/154,603, "Ultra-Dense LED Projector Using Thinned Gallium Nitride," (40231), which are all incorporated by reference in their entireties. The femtoprojector is located in the center of the contact lens, so the substrate has a narrow bridge 423 that extends from the main band of facets 420 to the island 424 that carries the femtoprojector devices 414. Because the substrate is flexible, the bridge 423 may be bent to conform to the contact lens shape. As shown in FIG. 4B, the island 424 has an aperture 424X. The LED frontplane is on one side of the island 424 while the femtoprojector optics is on the other side of the island 424. The aperture 424X allows light from the LED frontplane to enter the femtoprojector optics.

This example also includes an outward-facing imager, which is mounted on an extension tab 429. For example, see U.S. patent application Ser. No. 15/886,398, "Eye-Mounted Device Including a Femtocamera and Femtoprojector," (37924), which is incorporated by reference in its entirety. Semiconductor device 419 is the electronics for the imager, such as detector array and processing. If the imager were mounted directly on the existing facet 4201, it would be tilted too far off-axis and may also be blocked by the user's eyelids if positioned too far to the periphery. As a result, facet 4201 is shortened (its inner edge is offset relative to the other facets), and a flat extension tab 429 extends radially from the facet 4201. Bending at edge region 428 allows tab 429 to be tilted at a different angle than the main facets 420, so that the imager's field of view is more on-axis. The imager optics are on one side of the substrate 429 while the electronics 419 are on the other, with aperture 429X between the two.

The electronics assembly in this example also includes a processor 412 and RF filter 413. The substrate also includes flat extension tabs 445 to carry the coil 145. These tabs 445 extend radially from the main facets 420 with a bend in between. The holes allow casting resin to flow through the flexible circuit board and around the coil wires.

FIG. 4 shows the electronics assembly after folding into shape. FIG. 5 is a posterior view of the electronics assembly before folding. The substrate 310 is a flexible, flat circuit board. The circuit board may have conductive traces on only one side. Alternatively, it may have a non-conductive core, with conductive traces on both sides of the core and vias between the two sides of the core. It may also be a multi-layer board. The approximate boundaries of regions that will remain flat after bending are shown by the dashed lines.

The substrate is initially fabricated flat. Components may be placed on the substrate, bonded to it, and electrically tested while the assembly is flat. Semiconductor devices may be mounted on the flat facets using conventional techniques, such as surface mounting or flip-chip mounting. Anisotropic conductive paste (ACP) may also be used to attach semiconductor devices to the substrate. Components may be mounted to either side of the facets or to both sides. Alternatively, the facet may contain a cutout with the component positioned in the cutout. In this way, the total thickness is just the thickness of the component, rather than the thickness of the component plus the thickness of the substrate. In one approach, these components are flip-chip bonded along one edge and the remaining edges are glued with ACP to stabilize the position of the component in the cutout.

Figure 6A:
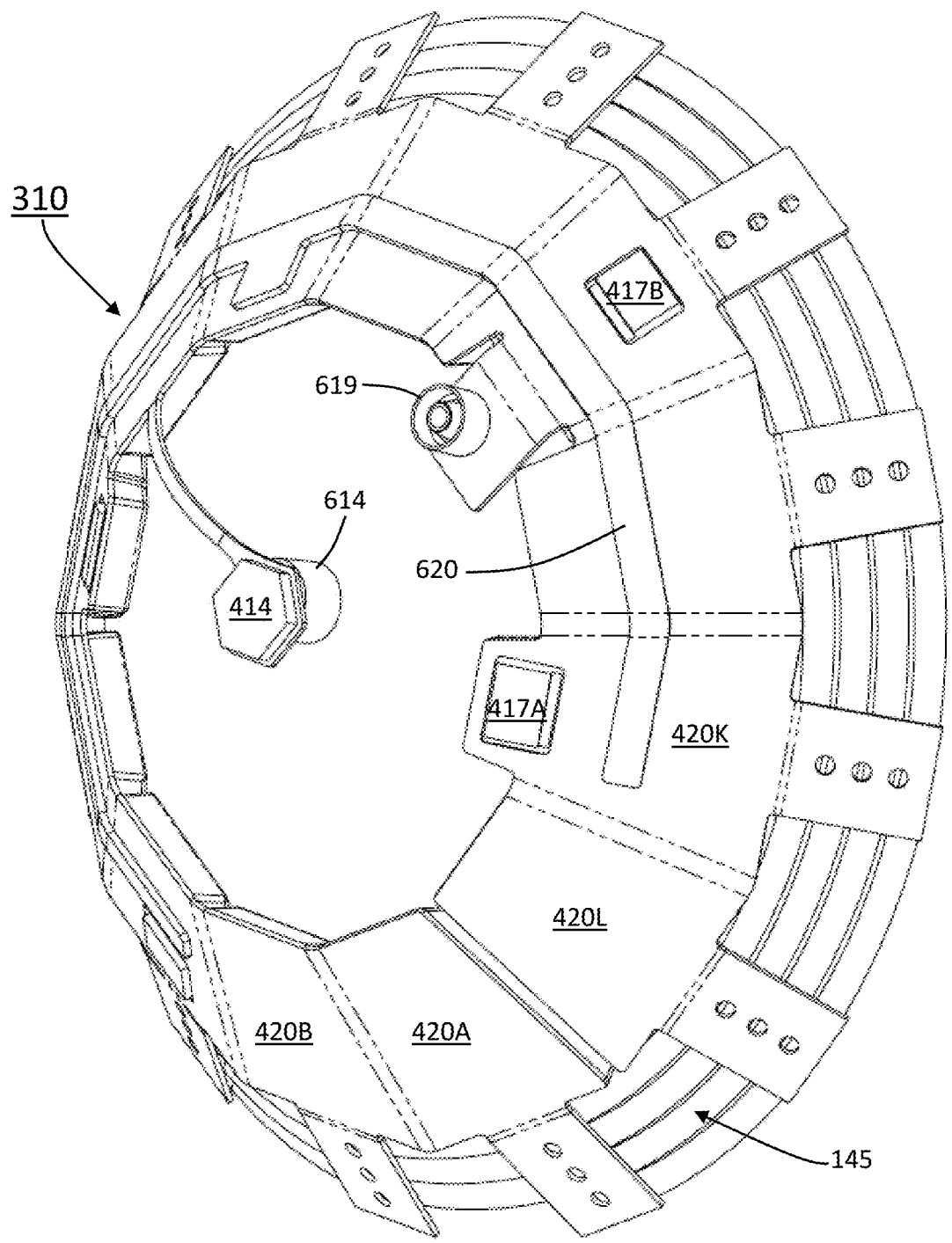
FIGS. 6A and 6B are anterior and posterior perspective views showing the electronics assembly of FIG. 3, with a coil and overmolding.
Figure 6B:
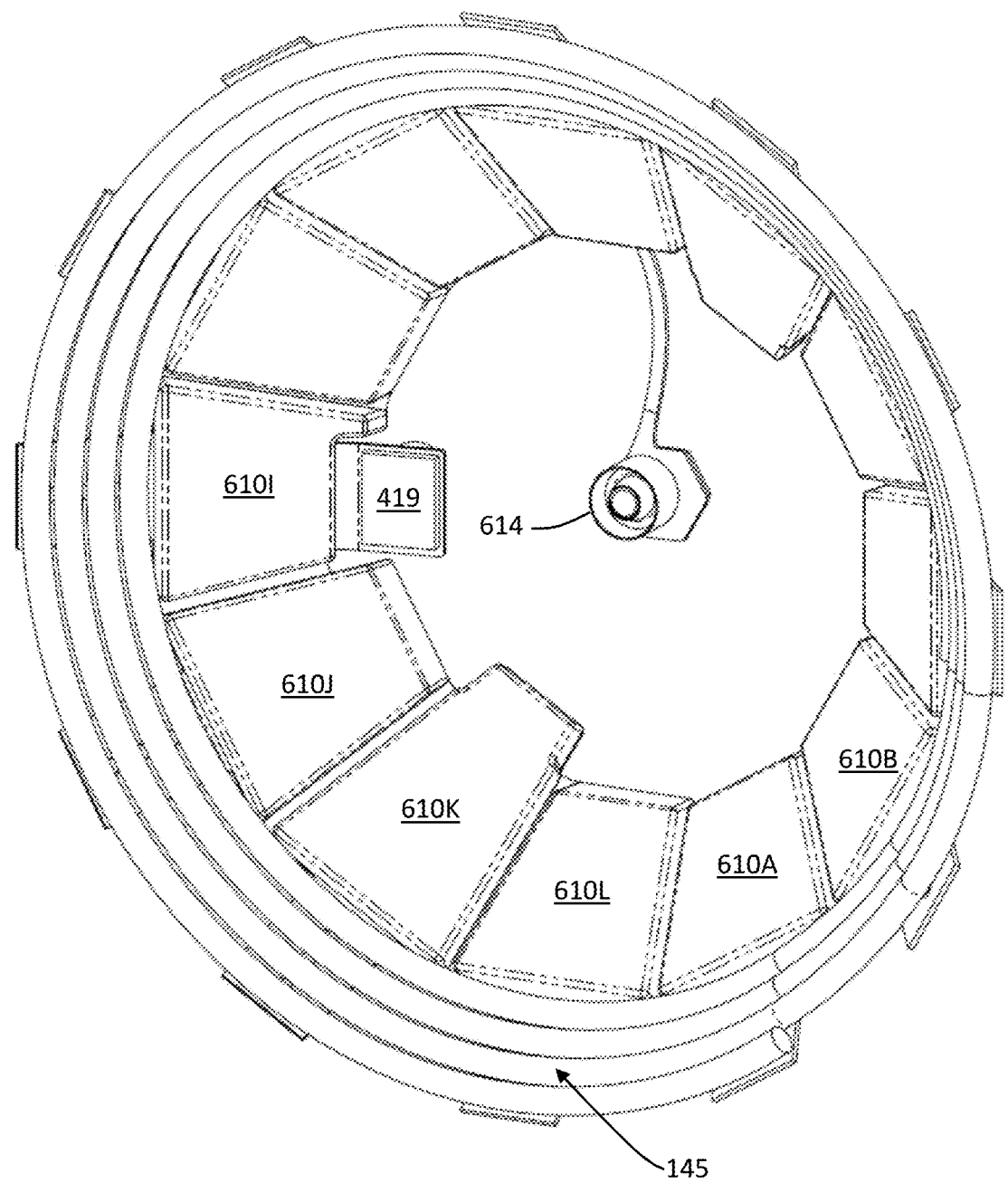

FIGS. 6A and 6B are anterior and posterior perspective views showing the electronics assembly of FIG. 3, with a coil and overmolding. Here, compared to FIG. 4, the femtoprojector optics 614 and imager optics 619 have been mounted onto the substrate. The coil 145 has also been mounted onto the substrate.

As more clearly seen in FIG. 6B, overmolding 610A-L is also added to the facets. After the components are mounted on the flat substrate of FIG. 5, the facets 420 are overmolded with a polymer. The polymer may be designed to have specific stiffness, dimensional stability, adhesion, and/or moisture sealing properties. The overmolding adds stiffness to the flat facets carrying the electrical components. The electronics assembly is then folded into a conical shape to fit inside the contact lens.

The polymer overmolding 610 ensures that each facet remains flat and isolated from the surrounding environment. All bonds from chips to the bus are on flat sections and they are protected from mechanical stress. This overmolding 610 encapsulates the electrical components mounted on the facets 420. It protects the components. It also adds stiffness to the flat facets, to further prevent unwanted bending of the flat facets, particularly in locations where electrical components are mounted. Other types of stiffeners may also be used. FIG. 6A also shows an antenna 620. Alternatively, the antenna may be implemented as a conductive pattern on the circuit board.

The outward-facing (anterior) surfaces of the electronics assembly may be colored to match the coloring and markings of a person's eye, thereby making the contact lens appear more natural when worn.

FIGS. 4-6 show one example. Other variations will be apparent. For example, each facet may be the same size and shape as all the others, or some of the facets may have sizes and shapes different from the others, or all the facets may be different sizes and shapes. The inner and outer edges of each facet may be different distances from the center of the contact lens. The electrical components may be mounted on the anterior side of the facets, on the posterior side or on both sides.

The tilt angles of the facets and their sizes may be adjusted to accommodate components of different sizes within the confines of the contact lens. Facets may be arranged to lie at specific angles with respect to each other after the substrate is folded into its three-dimensional shape or with respect to the contact lens. For example, in one design, three facets, spaced apart by 120 degrees in azimuth, lie in mutually perpendicular orientations when the substrate is folded to its final shape. This type of configuration is useful for eye tracking.

The facets may be based on non-regular frustums. Alternatively, they may be based on multiple frustums. For example, the facets may alternate between two different tilt angles. The odd facets may be based on a frustum with steeper sides and the even facets based on a frustum with less steep sides. Adjacent facets still meet at edge regions, but the edges may be skewed relative to the central axis of the contact lens, and odd and even facets may have different shapes. Different components may have different requirements on their position within the contact lens or their tilt angle relative to the contact lens central axis. The facets may be designed to meet these requirements. Components may also have different sizes and shapes. Some facets may be larger to accommodate larger components.

The band of facets may also have different designs. It does not have to cover a full 360 degrees of arc. It may form substantially less than a full annulus. In FIGS. 4-6, facets 420A-B do not carry any electrical components other than the coil. They may be omitted if the coil 145 is supported some other way. There may be multiple bands. The band may be narrower or wider or less uniform in width. Different facets may also have different widths.

Figure 7A:
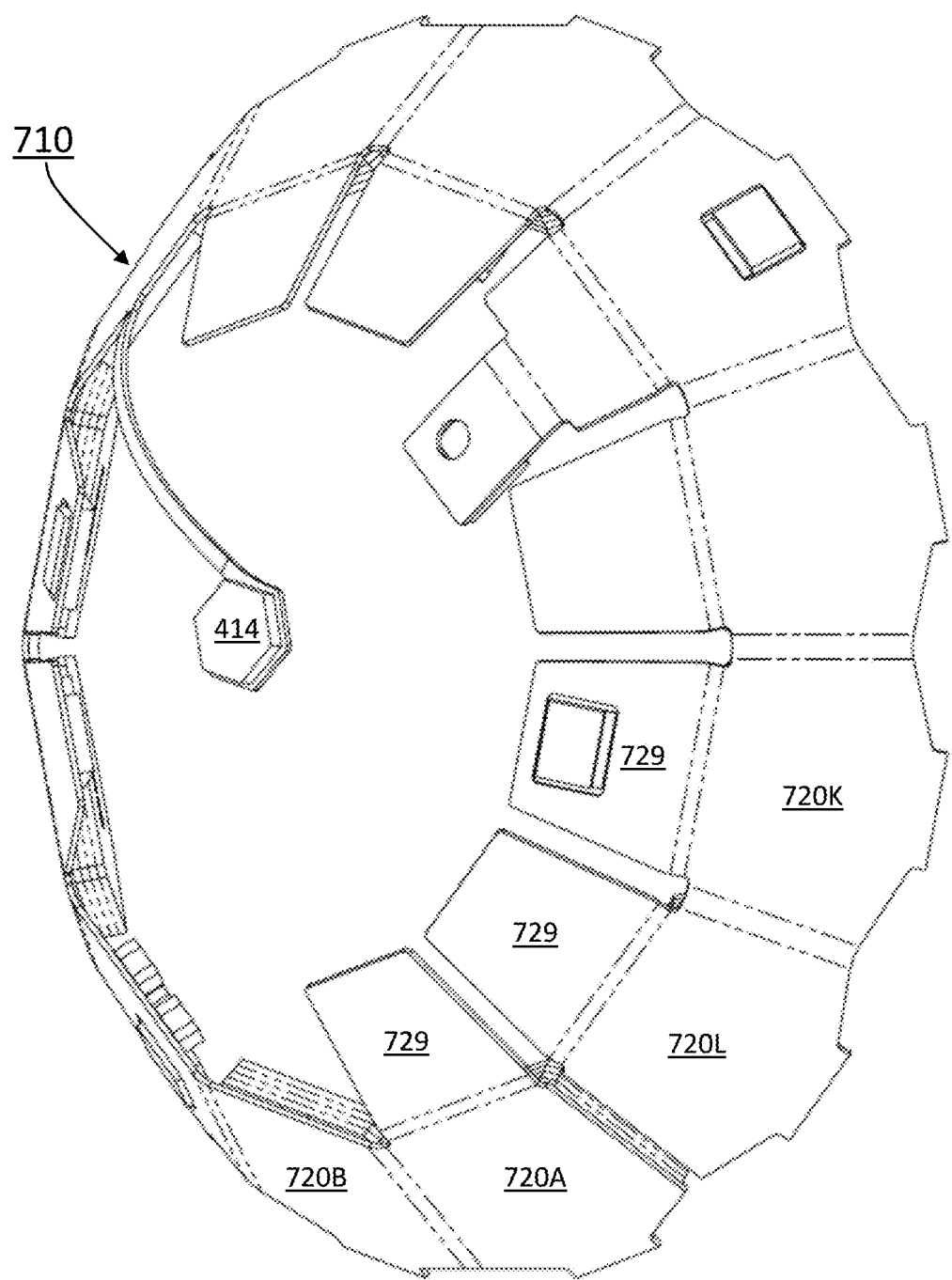
FIGS. 7A and 7B are anterior and posterior perspective views showing another electronics assembly.
Figure 7B:
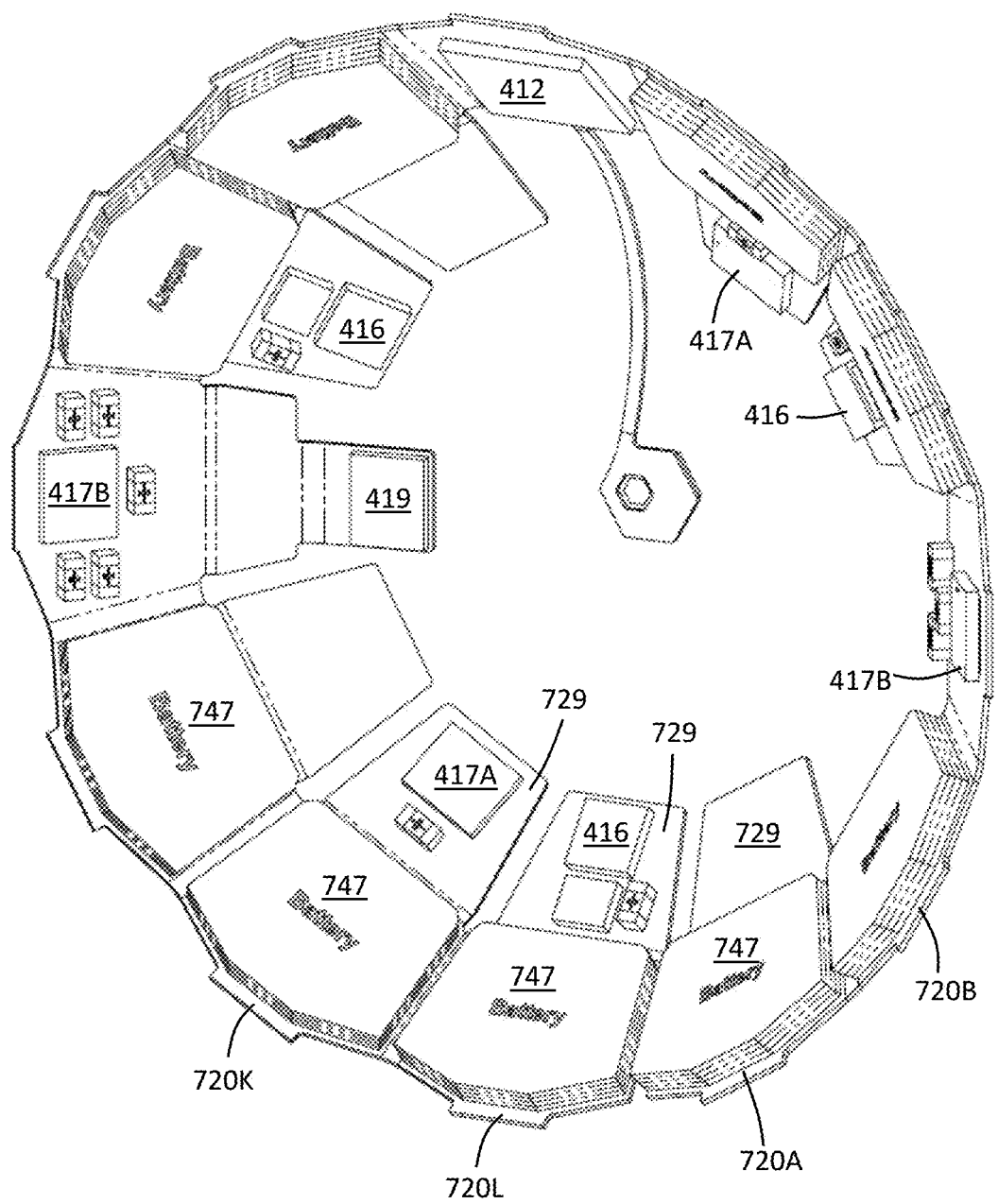

FIGS. 7A and 7B are anterior and posterior perspective views showing another electronics assembly. In this example, the non-planar substrate 710 includes a band of twelve flat facets 720A-L. Many of these facets carry batteries 747, as shown in FIG. 7B. Extension tabs 729 extend towards the center of the contact lens. These extension tabs 729 carry many of the electrical components that were carried by the main facets in FIGS. 4-6. The electrical components labeled with 4xx numbers in FIG. 7 are the same as in FIG. 4. Compared to FIG. 6, the design in FIG. 7 has a larger center opening, which may allow for better peripheral vision.

Figure 8:
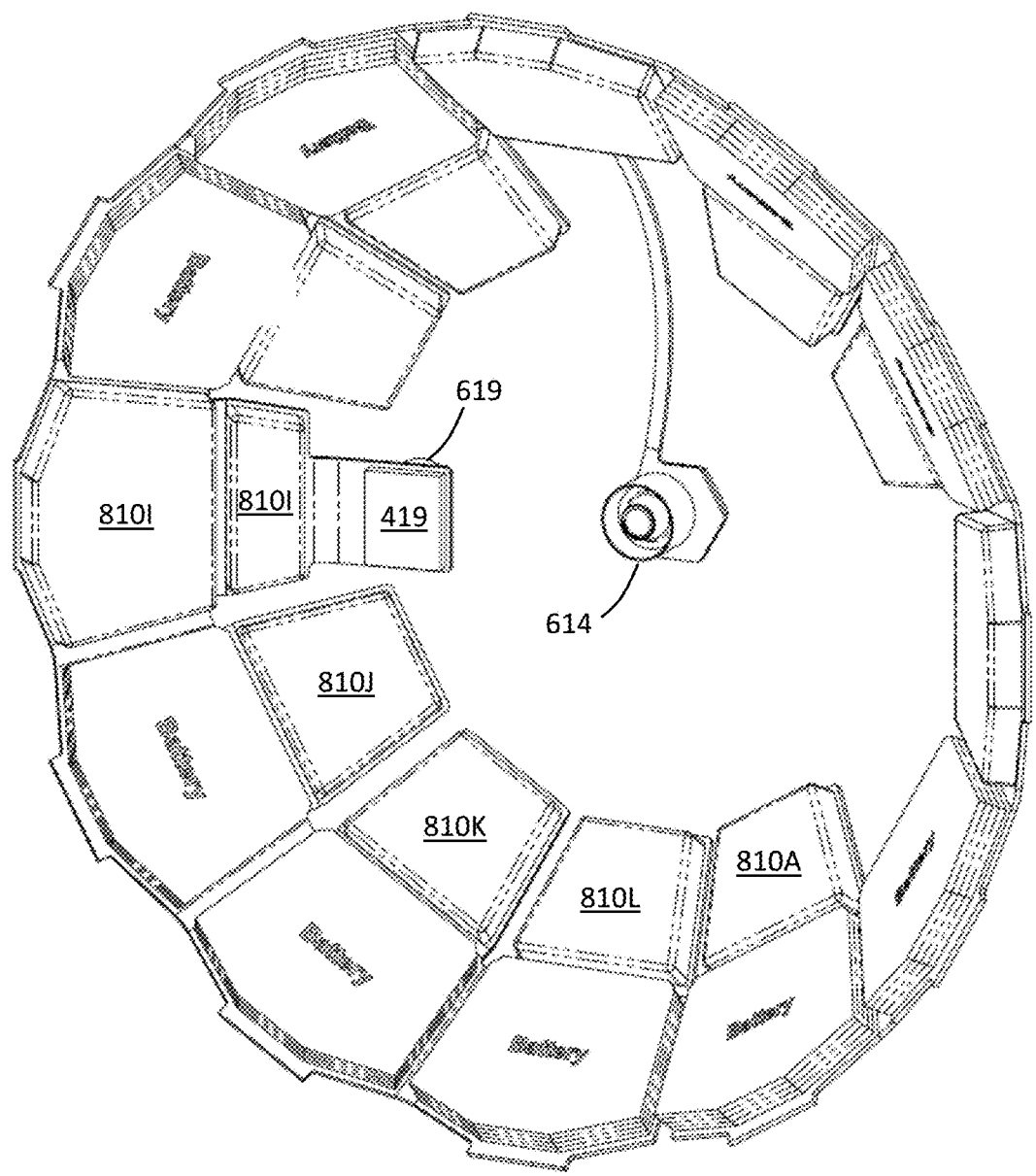
FIG. 8 is a posterior perspective view showing the electronics assembly of FIG. 7, with overmolding.

FIG. 8 is a posterior perspective view showing the electronics assembly of FIG. 7, with overmolding. The femtoprojector optics 614 and imager optics 619 have been added. The semiconductor devices have been overmolded 810.

Figure 9A:
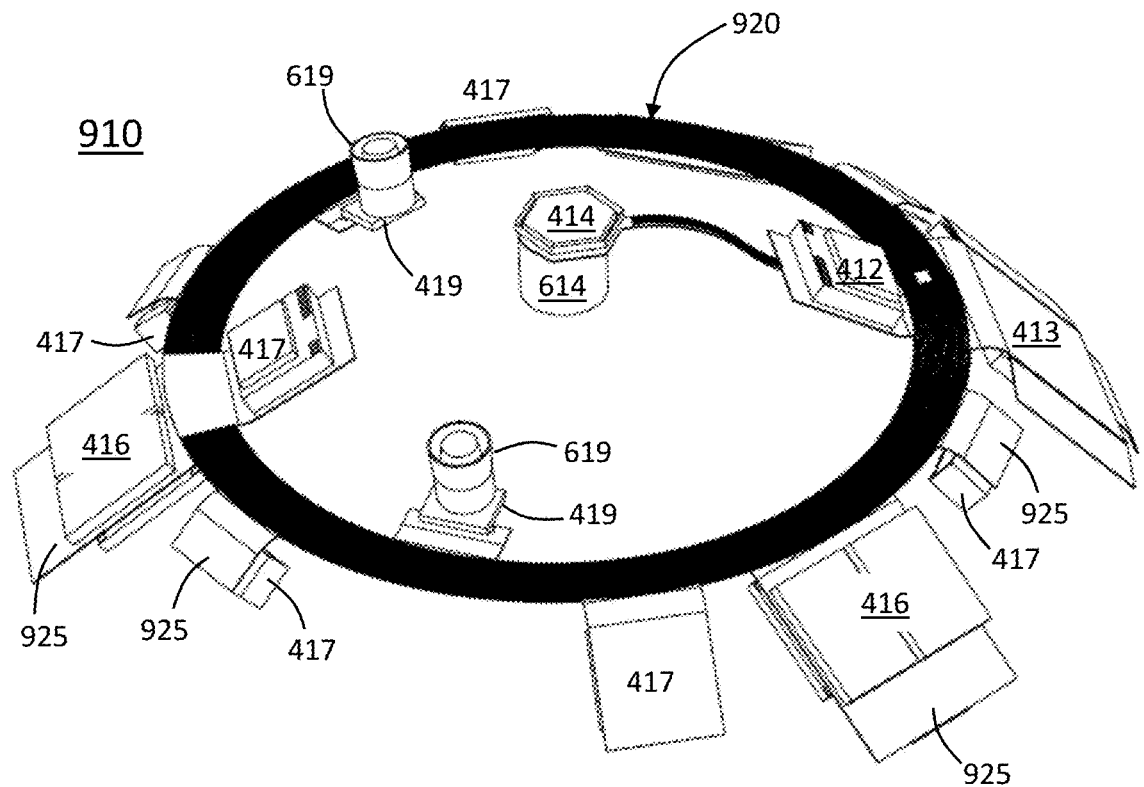
FIGS. 9A and 9B are an anterior perspective view and partial cross-sectional view of yet another electronics assembly.
Figure 9B:
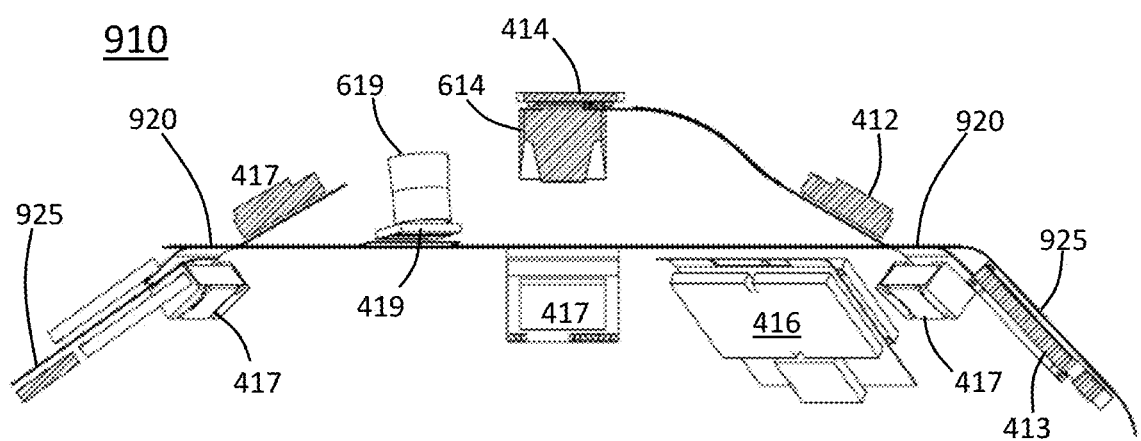

FIG. 9A is an anterior perspective view showing yet another electronics assembly. FIG. 9B is a partial cross-sectional view of the electronics assembly. In this design, the non-planar substrate 910 has a flat annular core portion 920. Flat tabs 925 extend radially from the annular core 920, and electrical components are mounted on these tabs 925. In one approach, the tabs 925 and core 920 meet at bendable edge regions. Thus, the overall substrate 910 may be fabricated flat, including conductive traces that provide electrical connections to the electrical components. Components may be placed on the substrate, bonded to it, and electrically tested while the assembly is flat. Optics and overmolding may be added. The entire assembly may then be folded into a three-dimensional shape to fit in a contact lens.

This example shows many of the same components as the previous examples. It includes femtoprojector electronics 414 and optics 614, and imager electronics 419 and optics 619. It also includes magnetometers 416 and accelerometers 417, processor 412 and RF filter 413. Additional tabs (not shown) may be used to carry a coil or batteries.

In alternate approaches, the tabs 925 may be separates pieces from the core 920 and later attached to the core 920.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. A non-planar substrate comprising a flexible circuit board bent into a three-dimensional shape that fits inside an electronic contact lens designed to be worn on a human eye, the three-dimensional shape including a three-dimensional annular band of flat facets configured to carry electrical components, wherein the flat facets meet at edge regions, with bending of the flexible circuit board at the edge regions between the flat facets.

2. The non-planar substrate of claim 1 wherein the circuit board comprises conductive traces that provide electrical connections to the electrical components.

3. The non-planar substrate of claim 2 wherein the circuit board comprises a non-conductive core with two sides, conductive traces on both sides of the core, and vias between the two sides of the core.

4. The non-planar substrate of claim 1 further comprising: overmolding of the flat facets that carry electrical components, wherein the overmolding adds stiffness to the flat facets, encapsulates the electrical components, and isolates the electrical components from a surrounding environment within the contact lens.

5. A non-planar substrate comprising a flexible circuit board bent into a three-dimensional shape that fits inside an electronic contact lens designed to be worn on a human eye, the three-dimensional shape including a band of flat facets configured to carry electrical components, wherein the three-dimensional shape further comprises a flat extension tab that extends radially from one of the flat facets and is not coplanar with said flat facet, wherein the extension tab is configured to carry an electrical component.

6. The non-planar substrate of claim 1 wherein the electrical components include semiconductor devices that are surface mounted or flip-chip mounted onto the flat facets of the circuit board.

7. A non-planar substrate comprising a flexible circuit board bent into a three-dimensional shape that fits inside an electronic contact lens designed to be worn on a human eye, the three-dimensional shape including a band of flat facets configured to carry electrical components, wherein the electrical components include semiconductor devices that are surface mounted or flip-chip mounted onto the flat facets of the circuit board and at least one of the flat facets includes a cutout to permit the semiconductor device mounted on the flat facet to protrude through the flat facet.

8. The non-planar substrate of claim 6 wherein some of the semiconductor devices are mounted onto an anterior side of the flat facets and others of the semiconductor devices are mounted onto a posterior side of the flat facets.

9. The non-planar substrate of claim 1 wherein the electrical components include a coil.

10. The non-planar substrate of claim 1 wherein the flat facets in the band all have a same shape.

11. The non-planar substrate of claim 1 wherein the flat facets in the band alternate between two different shapes.

12. The non-planar substrate of claim 1 wherein the flat facets in the band are all either triangular or quadrilateral in shape.

13. The non-planar substrate of claim 1 wherein the band contains twelve facets that form substantially a full annulus, and the electrical components comprise a first pair of accelerometers mounted on opposing facets and a second pair of accelerometers also mounted on opposing facets, wherein no two of the accelerometers are mounted on adjacent facets.

14. The non-planar substrate of claim 1 wherein the band contains twelve facets that form substantially a full annulus, and the electrical components comprise three magnetometers that are mounted on every fourth facet.

15. The non-planar substrate of claim 1 wherein the band forms substantially less than a full annulus.

16. The non-planar substrate of claim 1 wherein at least one of the flat facets is positioned at a tilt angle determined by a function of the electrical component mounted on said flat facet.

17. The non-planar substrate of claim 1 wherein at least two of the flat facets have different radial widths.

18. The non-planar substrate of claim 1 wherein the band of flat facets is opaque but is positioned such that the band does not substantially block light from entering the eye through the contact lens.

19. An electronics assembly comprising:
a set of semiconductor devices configured for use in an electronic contact lens designed to be worn on a human eye;
a flat flexible circuit board comprising a band of facets, wherein the semiconductor devices are mounted on the facets and conductive traces on the circuit board provide electrical connections to the semiconductor devices, and the flat flexible circuit board is bendable into a three-dimensional annular shape that fits inside an electronic contact lens, wherein the facets meet at edge regions with bending of the flexible circuit board at the edge regions between the facets; and
overmolding of the facets that carry the semiconductor devices, wherein the overmolding provides additional stiffness to the flat facets, encapsulates the semiconductor devices, and isolates the semiconductor devices from a surrounding environment within the contact lens.

20. An electronic contact lens comprising a contact lens that contains:
a set of semiconductor devices;
a non-planar substrate comprising a flexible circuit board bent into a three-dimensional annular shape that fits inside an electronic contact lens, the three-dimensional annular shape including a band of flat facets meeting at edge regions, with bending of the flexible circuit board at the edge regions between the flat facets, wherein the semiconductor devices are mounted on the flat facets and conductive traces on the circuit board provide electrical connections to the semiconductor devices; and
overmolding of the flat facets that carry the semiconductor devices, wherein the overmolding provides additional stiffness to the flat facets, encapsulates the semiconductor devices, and isolates the semiconductor devices from a surrounding environment within the contact lens.

21. A non-planar substrate that carries one or more electrical components contained in an electronic contact lens designed to be worn on a human eye, the substrate comprising a flexible circuit board bent to form a three-dimensional shape that fits inside an electronic contact lens, the three-dimensional shape comprising:
  a flat annular core portion; and
  one or more flat tabs that extend radially from the flat annular core portion, wherein the flat tabs are not coplanar with the flat annular core portion and the flat tabs are configured to carry electrical components.

22. The non-planar substrate of claim 21 wherein the circuit board further comprises conductive traces that provide electrical connections to the electrical components.

23. The non-planar substrate of claim 1 wherein the three-dimensional annular band of flat facets is less than a full annulus.

* * * * *